US011998231B2

(12) United States Patent
Kronström et al.

(10) Patent No.: US 11,998,231 B2
(45) Date of Patent: Jun. 4, 2024

(54) APPARATUS AND METHOD FOR MECHANICALLY DISINTEGRATING TISSUE INTO MICROGRAFTS, AND FEEDER PIECE USED IN CONNECTION WITH THE DISINTEGRATION OF TISSUE

(71) Applicant: EPIHEART OY, Helsinki (FI)

(72) Inventors: Kai Kronström, Espoo (FI); Aleksi Kuuva, Helsinki (FI); Esko Kankuri, Helsinki (FI)

(73) Assignee: EPIHEART OY, Helsinki (FI)

( * ) Notice: Subject to any disclaimer, the term of this patent is extended or adjusted under 35 U.S.C. 154(b) by 0 days.

(21) Appl. No.: 18/033,946

(22) PCT Filed: Oct. 14, 2021

(86) PCT No.: PCT/IB2021/059433
§ 371 (c)(1),
(2) Date: Apr. 26, 2023

(87) PCT Pub. No.: WO2022/090848
PCT Pub. Date: May 5, 2022

(65) Prior Publication Data
US 2023/0301680 A1    Sep. 28, 2023

(30) Foreign Application Priority Data
Oct. 26, 2020   (FI) ..................... 20206060

(51) Int. Cl.
*A61B 17/322*   (2006.01)
(52) U.S. Cl.
CPC .... *A61B 17/322* (2013.01); *A61B 2017/3225* (2013.01)

(58) Field of Classification Search
CPC ......... A61B 17/322; A61B 2017/3225; C12M 45/02; C12M 3/08; G01N 2001/2866;
(Continued)

(56) References Cited

U.S. PATENT DOCUMENTS 4,413,059 A * 11/1983 Tihon ..................... A01H 4/001
435/283.1
2003/0116664 A1    6/2003 Castronovo
(Continued)

FOREIGN PATENT DOCUMENTS

DE         19600686 C1    2/1997
WO     2016/097960 A2    6/2016

OTHER PUBLICATIONS

International Search Report and Written Opinion for International Application No. PCT/IB2021/059433, mailed on Feb. 4, 2022, 11 pgs.

*Primary Examiner* — Anh T Dang
(74) *Attorney, Agent, or Firm* — Robert P. Michal; Carter, DeLuca & Farrell LLP

(57) ABSTRACT

For improving the quality of grated tissue, a method is presented for mechanically disintegrating tissue (2) into micrografts, in which method a blade part (3), which has a planar grater surface (3.1), and the tissue placed in a tissue holder are made to move relative to each other, and where the tissue is guided against the grater surface (3.1), characterised in that the tissue is guided against the grater surface (3.1) together with the tissue feeder piece so that the feeder piece (12) is disintegrated together with the tissue (2). The application also includes independent claims concerning an apparatus for mechanically disintegrating tissue into micrografts, and a feeder piece.

20 Claims, 6 Drawing Sheets

Figure 1:
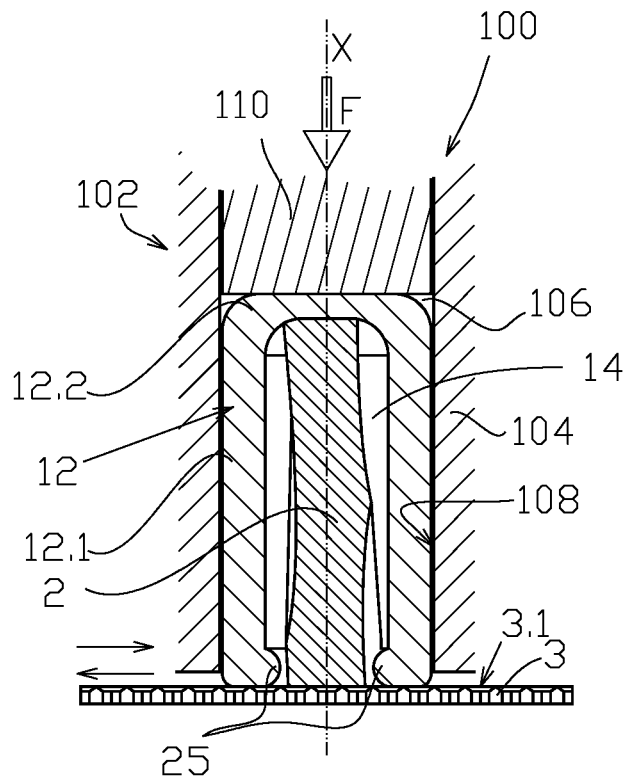

(58) Field of Classification Search
CPC ............ G01N 2001/2873; G01N 1/286; B02C 18/30; B02C 18/365
See application file for complete search history.

(56) References Cited

U.S. PATENT DOCUMENTS

2014/0342394 A1\* 11/2014 Parker ................ G01N 33/5088
　　　　　　　　　　　　　　　　　　　　　　　435/402
2023/0081048 A1\* 3/2023 Oliner ...................... G01N 1/06
　　　　　　　　　　　　　　　　　　　　　　　422/536

\* cited by examiner

APPARATUS AND METHOD FOR MECHANICALLY DISINTEGRATING TISSUE INTO MICROGRAFTS, AND FEEDER PIECE USED IN CONNECTION WITH THE DISINTEGRATION OF TISSUE

FIELD OF INVENTION

The invention concerns an apparatus according to the preamble of the independent claim for mechanically disintegrating tissue into micrografts.

BACKGROUND OF INVENTION

Medical treatments and/or biological studies involve situations where tissue is taken from its original location and the tissue is used for growing new cells and/or tissue somewhere else. It is often advantageous to cut the original tissue into smaller parts. Such small pieces of tissue are referred to as micrografts here. Micrografts may only contain one cell, but typically they contain a group of cells. The diameter of an individual micrograft is typically a few dozen or hundred micrometres. The advantage of micrografts is that more units and area, which are in direct interaction with the surroundings, are obtained from the same tissue mass. The cutting of tissue may also be expedient for various laboratory examinations, such as genetic analyses.

Tissue can be cut using several different methods. One known example is described in U.S. Pat. No. 7,708,746: Method and apparatus for processing dermal tissue, which describes a cutting assembly with a plurality of blades. Other examples of solutions for cutting tissue have been presented in the following publications, among others: WO2014039697A1; TISSUE PROCESSING APPARATUS AND METHOD FOR PROCESSING ADIPOSE TISSUE and WO02088296A1 MULTICHAMBER DEVICE AND USES THEREOF FOR PROCESSING OF BIOLOGICAL SAMPLES. There are also several known chemical methods for releasing cells from each other.

However, publications best describing prior art are U.S. Pat. No. 5,731,199A; Mechanical triturator for biological material and in particular WO2016/097960 A2; DISREGATING DEVICE OF BIOLOGICAL MATERIAL AND CORRESPONDING MANUFACTURING METHOD AND METHOD FOR THE PREPARATION OF CELL SUSPENSIONS AND TISSUE MICROGRAFTS.

One challenge with known solutions, as presented in publication WO2016/097960 A2, for example, is that a typically steel rotor in practice chafes against a sharp-edged blade surface, which can also be referred to as a grater surface, in which case metal particles may become rubbed off from the blade surface (grater blade) into the tissue suspension. If there was a gap between the grater plate and the rotor, with the gap used for removing such contact, the entire tissue would not, however, be processed, but some of it would remain between the blade surface and the rotor. This is a problem, because the amount of tissue processed is often small, and its precise use is expedient. It can be stated empirically that in some practical solutions both of the above-mentioned problems become reality, in which case some metal is ground off into the suspension while at the same time the tissue is not processed entirely.

The objective of the invention is to accomplish an apparatus for mechanically disintegrating tissue into micrografts, with which apparatus it is possible to at least significantly reduce or to remove the above-mentioned problems. The objective of the invention can be formulated in other words as follows: how to enable the achievement of cleaner grated tissue.

Description of Invention

The objectives of the invention are achieved by means of an apparatus according to the independent claim 1, a method according to the parallel independent claim 12 and a feeder piece according to the parallel independent claim 20. The dependent claims describe the advantageous aspects of the apparatus, method and feeder piece.

An apparatus for mechanically disintegrating tissue into micrografts comprises a blade part, which has a grater surface, and a tissue holder for supporting the tissue and for guiding it against the grater surface, where these two are movable relative to each other, in which case the tissue holder comprises a guide space, which is arranged in the body part of the tissue holder, which guide space has at least one internal guide surface that is straight in the longitudinal direction of the guide space, which guide surface is at an angle with respect to the grater surface, and a tissue feeder piece, which is arranged in the guide space to be movable in the longitudinal direction, and the feeder piece comprises a hollow that is open at least from the grater surface side end, into which hollow the tissue is placeable, and where the feeder piece is made from a sacrificial material, in which case it is arranged to be grated at least partially into the micrograft obtained from the tissue, when the apparatus is used for disintegrating tissue.

By means of such apparatus, when the grater surface and the tissue are moved relative to each other, it is possible to process the tissue into micrografts effectively so that even small tissue samples can be utilised accurately.

The grater surface is essentially planar at least in the direction of movement of the movement between the tissue/feeder piece and the grater surface.

According to one advantageous embodiment of the invention, the body part is arranged to be at a distance from the grater surface, and the feeder piece is, when the apparatus is in operation, arranged against the grater surface. In this way, it is possible to utilise the available tissue almost completely in the process by means of the invention.

According to one advantageous embodiment of the invention, the guide space and its guide surface are cylindrical, and the feeder piece has a cylindrical outer surface.

According to one advantageous embodiment of the invention, the guide space and its guide surface have a cross section of a polygon, and the outer surface of the feeder piece has a cross section of a polygon.

According to one advantageous embodiment of the invention, the feeder piece comprises one or more walls, which define the hollow inside the feeder piece.

According to one advantageous embodiment of the invention, the feeder piece comprises one or more walls in the direction of the guide space, and an end part at the end opposite to the end on the side of the grater surface.

According to one advantageous embodiment of the invention, the end part is a fixed part of the feeder piece.

According to one advantageous embodiment of the invention, the feeder piece comprises a separate hollow cylindrical circumferential piece and a separate push piece, in which case the hollow of the feeder piece is cylindrical and the push piece is arranged to be movable inside the hollow of the circumferential piece in the longitudinal direction.

In this embodiment, different feeder pieces can also move relative to each other.

According to one advantageous embodiment of the invention, the apparatus comprises a feeding mechanism for directing a force to the feeder piece, which feeding mechanism is arranged to direct a force of a different magnitude to the push piece and to the circumferential piece.

In this embodiment, different feeder pieces can move relative to each other so that the circumferential piece is in a close and sufficient contact with the blade part, and the push piece is made to move at a speed that is suitable in view of the disintegration of the tissue.

According to one advantageous embodiment of the invention, the apparatus comprises a feeding mechanism for directing a force to the feeder piece.

Method for mechanically disintegrating tissue into micrografts, where in the method the blade part, which has a planar grater surface, and tissue placed in the tissue holder are made to move relative to each other, and where the tissue is guided against the grater surface together with the tissue feeder piece so that the feeder piece is disintegrated together with the tissue.

According to one advantageous embodiment of the invention, the tissue is disintegrated by pressing it against the grater surface until the bottom part, which belongs to the feeder piece, is in contact with the grater surface.

According to one advantageous embodiment of the invention, the feeder piece is formed from more than one parts, comprising a circumferential piece and a push piece, and such a force is directed to the circumferential piece that the piece is in a close and sufficient contact with the blade part, and such a force is directed to the push piece that it moves at a speed that is suitable in view of the disintegration of the tissue.

According to one advantageous embodiment of the invention, the feeder piece is a cylindrical piece, which comprises a cylindrical hollow, which is open from at least a first end, and an end part of the hollow, which end part plugs the hollow.

According to one advantageous embodiment of the invention, the feeder piece is of a material that comprises one or more of the following: various sugars, salts, calcium, and fillers of pharmaceuticals.

In the implementation according to the invention, tissue is pressed against the grater surface of the blade part by utilising a separate feeder piece, the material of which is intended to be grated at least partially into the micrograft as part of the process.

The apparatus and method according to the invention enable the processing of tissue into micrografts so that the micrograft is free from components that are detrimental in view of its upcoming processing. More precisely, by means of the invention it is possible to avoid the release of material from the blade part into the micrograft. In addition to this The apparatus and method according to the invention also enable that tissue can be transferred safely into people or used in other purpose.

In the implementation according to the invention, the grater surface and tissue are moved relative to each other. The suitable forces and speeds, with which the tissue and the grater surface are moved and pressed against each other, are selectable by using means suited to the purpose.

In the implementation according to the invention, the grater surface and the tissue are moved relative to each other, for example, so that the tissue is pressed against a rotating grater surface, or alternatively, the tissue is moved against a stationary grater surface.

The feeder piece is advantageously a hollow structure, inside which the actual tissue material is located. When the hollow feeder piece is pressed against the grater surface, which moves relative to the feeder piece, both the walls of the hollow feeder piece and the tissue itself are grated. A significant advantage in an implementation such as this is that all tissue is grated.

The material of the feeder piece is selected so that it is advantageously sufficiently hard to support the tissue but still so soft/fragile that the forces, which wear the blade part, are so small that practically no material becomes loose from the blade part. Such material is referred to as sacrificial material. Moreover, it is often advantageous that the selected material is removable later and/or it poses no disadvantage to the utilisation of micrografts.

Such feeder piece can be made, for example, from a suitable sugar material, gelatine or hypromellose.

The advantage of these materials is that they are available in pharmaceutical grade and that they have proven to be safe to a great extent. In this way, if the feeder piece material becomes part of the micrograft, this is not necessarily a disadvantage to the use of the micrograft.

Moreover, the sacrificial material can be partially or completely removable by washing. The washing can take place, for example, by adding salt solution into the micrograft—sacrificial material, by dissolving the sacrificial material into the salt solution and by separating the micrografts by centrifugation.

When the tissue moves relative to the grater surface and against it, the tissue has a tendency to get stuck to the grater surface. This phenomenon can be reduced by moistening the grater surface by salt solution, for example, which reduces friction and sticking. Water-based moistening can, however, cause softening of the sacrificial material and deterioration of the functioning of the feeder piece. To solve this problem, it is possible to use suitable—biocompatible—oil or alcohol, such as purified soy oil or glycerol, in connection with water-soluble sacrificial materials (such as hypromellose). In this case, the sacrificial material does not dissolve during the working stage, and these materials are available in pure and safe form. Purified soy oil, for example, is used as an intravenous nutrient (so-called intralipid), and glycerol has a good safety profile.

Correspondingly, the oil, grease, alcohol (such as glycerol) or liquid that is not soluble in water, which has been used for reducing friction, can be separated from a water-based micrograft mixture, by utilising, for example, centrifugation or some other known separation method, such as extraction or dissolution, which utilises physical differences between substances or their different phases.

The different embodiments of the invention can be varied to minimise the amount of the needed sacrificial material by means of support structures and/or a feeder piece with multiple parts. Moreover, the shapes of the feeder piece can be modified so that the handling of the tissue is facilitated.

In one embodiment of the invention, tissue that has potentially become stuck to the grater surface (or tissue that has escaped from inside the feeder piece but not yet completely grated) can be post-gnawed after the entire tissue has been grated. This takes place by means of the bottom part of the feeder piece.

The implementation according to the invention has a grater surface, which is implemented in some known manner. Various grater structures are known not only in the above-referenced patents but also in other areas, such as in meat grinders and cheese graters. In these, however, the grater surfaces are equipped with significantly larger grater elements.

The applications of the invention are in particular in medical treatments, where the patient's own tissue is transferred as part of the treatment. However, the invention is also applicable to areas where the transferred cells need to grow in a laboratory, for example, or when it is necessary to cut the tissue for laboratory analyses, for example.

The mechanical processing of tissue into micrografts is referred to using various terms such as disaggregation, cutting, and grinding or mincing, but also shredding/grating are descriptive terms, because they highlight the integrity of smaller units, at least to some degree. These terms can, however, be considered largely synonymous, despite the differences in what the terms highlight.

The solution according to the invention can accomplish the mechanical processing of tissue into micrografts by means of movement between the tissue and the grater surface as well as by means of a force that keeps the tissue and the grater surface in contact with each other.

LIST OF DRAWINGS

Figure 2:
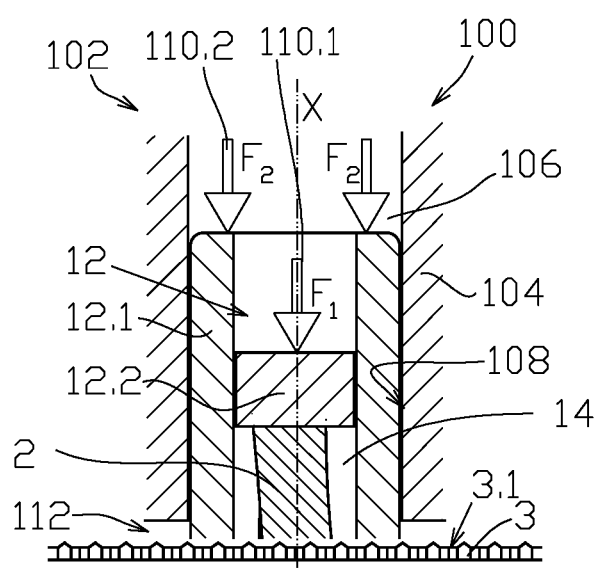
Figure 3:
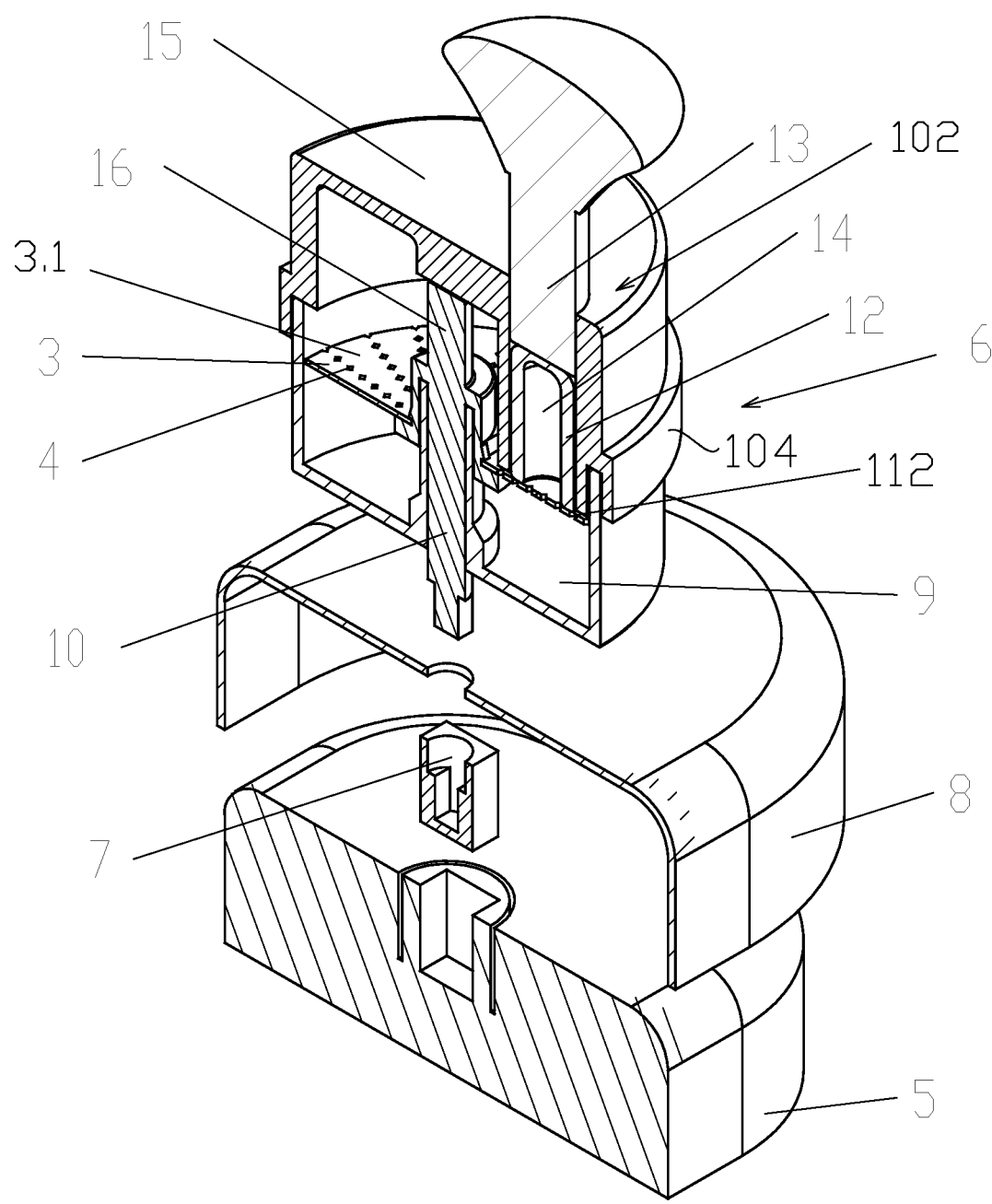
Figure 4:
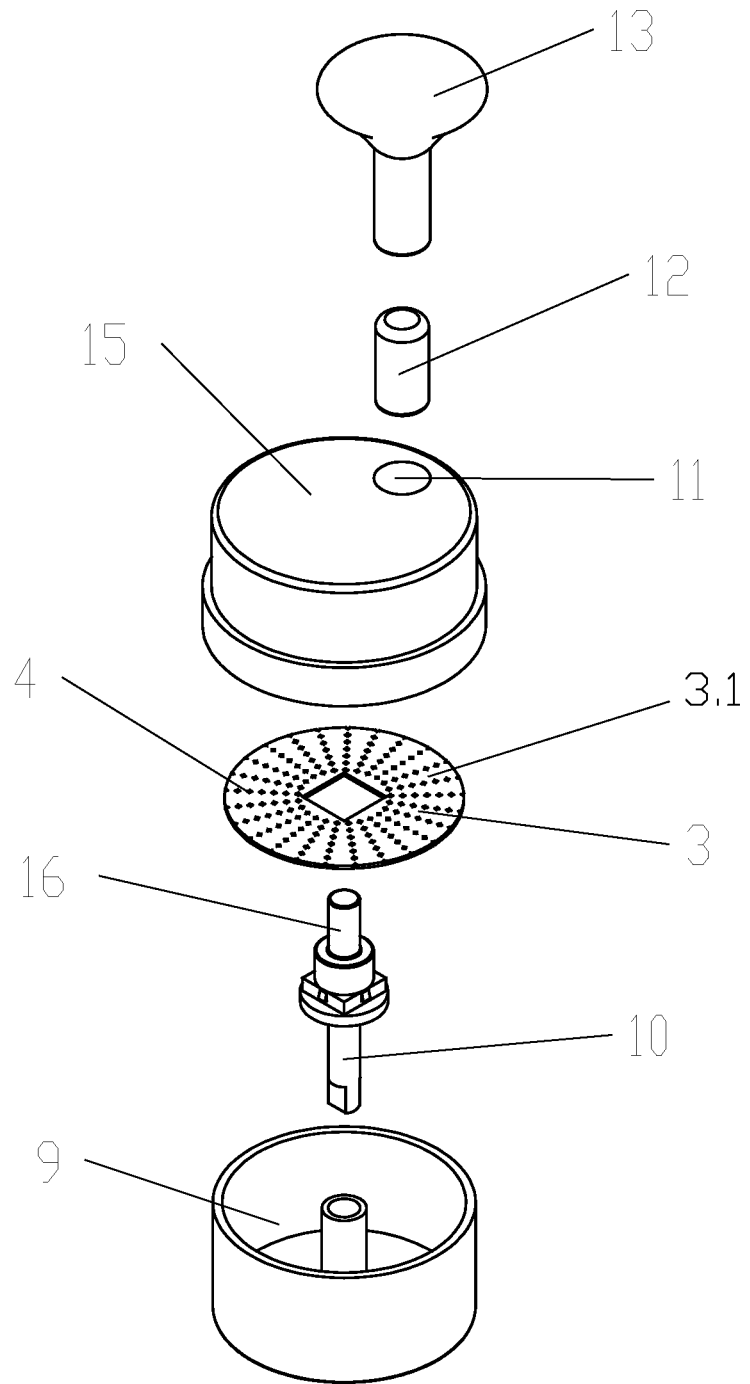
Figure 5:
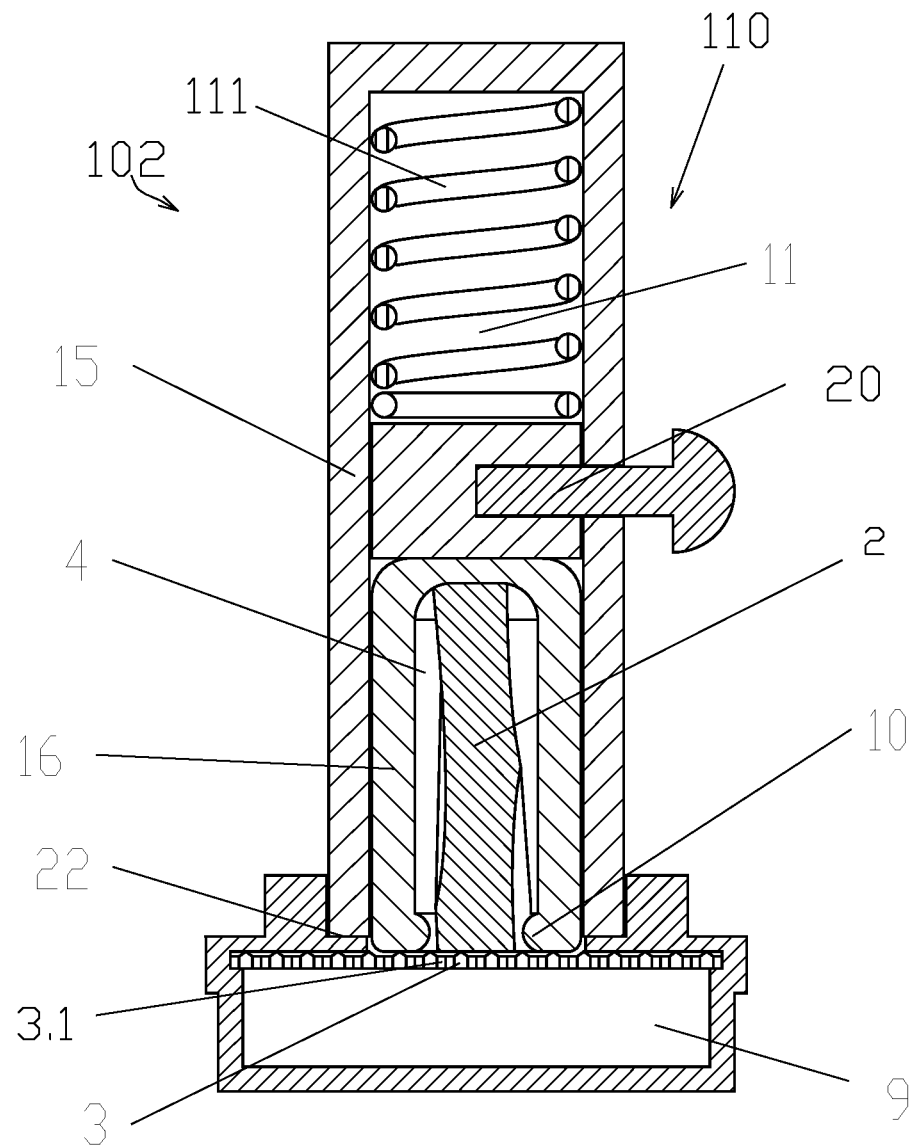
Figure 6:
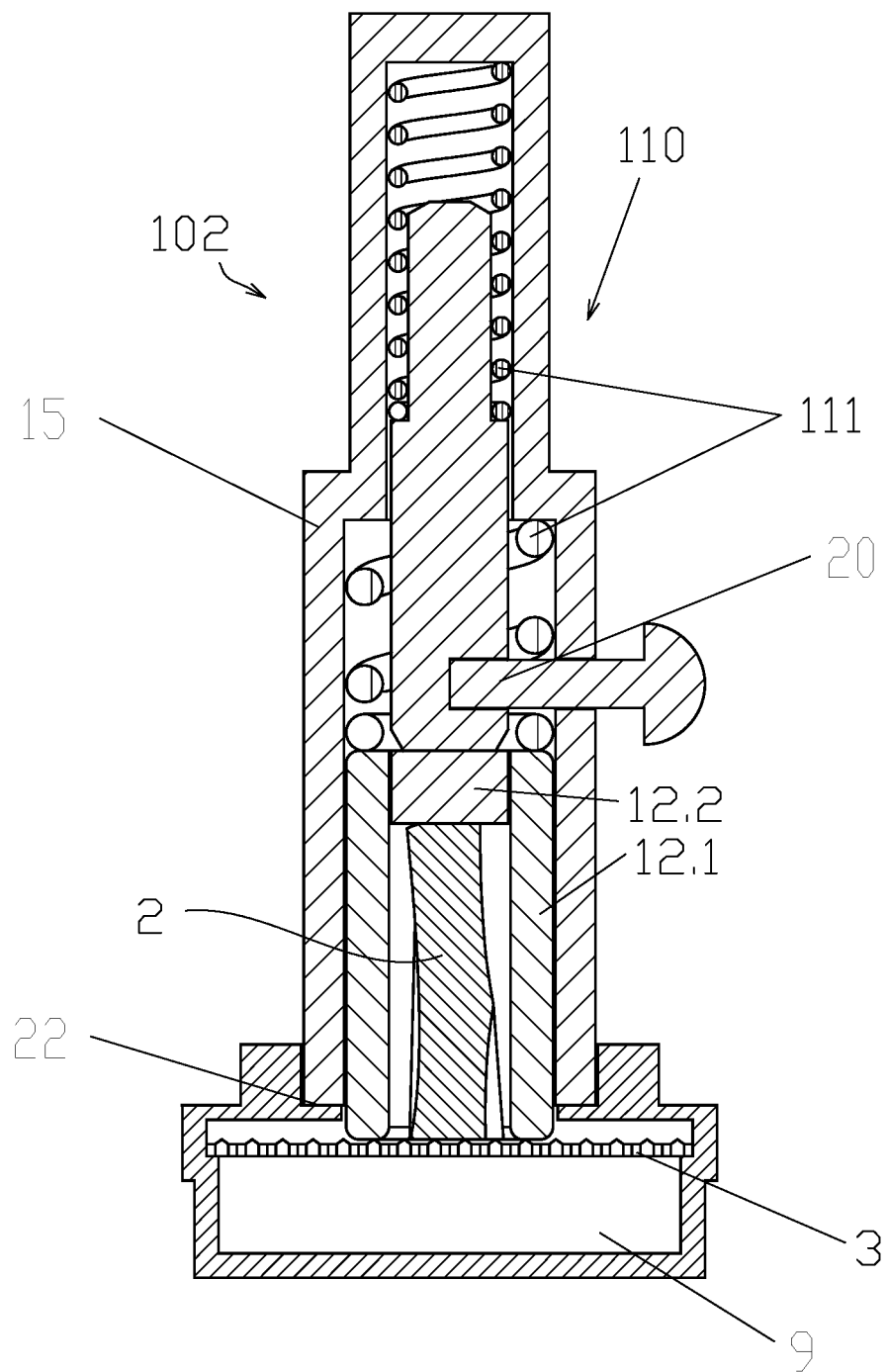
Figure 7:
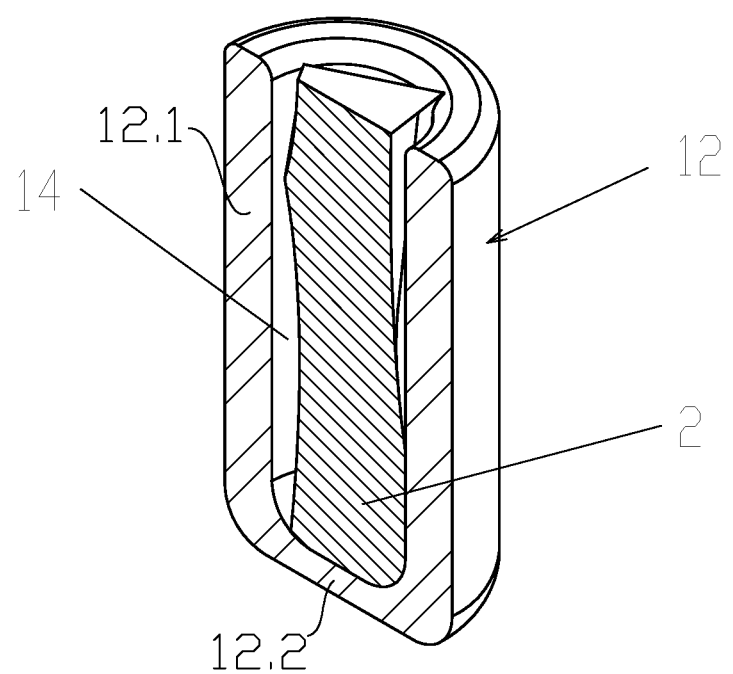

In what follows, the invention and its functioning are described by making reference to the enclosed schematic figures, where:

FIG. 1 shows schematically one embodiment of the apparatus according to the invention for mechanically disintegrating tissue into micrografts, FIG. 2 shows schematically another embodiment of the apparatus according to the invention for mechanically disintegrating tissue into micrografts, FIG. 3 shows schematically another embodiment of the apparatus according to the invention for mechanically disintegrating tissue into micrografts, FIG. 4 shows schematically another embodiment of the apparatus according to the invention for mechanically disintegrating tissue into micrografts, FIG. 5 shows schematically yet another embodiment of the apparatus according to the invention for mechanically disintegrating tissue into micrografts, FIG. 6 shows schematically yet another embodiment of the apparatus according to the invention for mechanically disintegrating tissue into micrografts, and FIG. 7 shows schematically yet another embodiment of the feeder piece according to the invention.

DETAILED DESCRIPTION OF THE DRAWINGS

FIG. 1 show schematically one embodiment of the apparatus 100 according to the invention for mechanically disintegrating tissue into micrografts. The apparatus comprises a blade part 3 with a planar grater surface 3.1 and a tissue holder 102 for supporting tissue 2 and guiding it against the grater surface 3.1 of the blade part. The blade part 3 and the tissue holder 102 are arranged to be movable relative to each other, in which case the planar grater surface 3.1 is straight at least in the direction of the movement between the blade part 3 and the tissue holder 102. There are various ways in which to accomplish the relative movement between the blade part 3 and the tissue holder.

The tissue holder 102 comprises a body part 104 in the embodiment according to FIG. 1. A guide space 106 is arranged in the body part 104 for taking the tissue against the grater surface 3.1. The guide space 106 has at least one guide surface 108, against which the tissue 2 is supported by means of a specific feeder piece 12. The guide surface is straight in its longitudinal direction X. The guide surface and the feeder piece can have many types of cross-sectional shapes. Although a circular shape is advantageous, the cross section can also be a polygon.

The guide space 106 of the tissue holder, in other words its longitudinal direction X is at an angle with respect to the plane of the blade part, advantageously approximately at a right angle. In other words, the angle can be other than a right angle. The dimensions of the guide space are such that its longitudinal dimension is bigger than the cross-sectional dimension.

In other words, the tissue holder 102 of the apparatus 100 comprises a feeder piece 12, and it is arranged in the guide space 106 to be movable at least in the longitudinal direction. The feeder piece 12 comprises a hollow 14 at least at the grater surface 3.1 side end, into which hollow 14 the tissue 2 is placeable. The hollow extends almost through the feeder piece 12 in its longitudinal direction. The hollow ends at the bottom part 12.2 of the feeder piece. In the embodiment of FIG. 1, the feeder piece 12 is of a single part, and it includes a circumferential part 12.1 and a bottom part 12.2. In other words, the feeder piece is cup-like in the embodiment presented in FIG. 1. FIG. 1 shows an alternative additional feature, according to which structures 25, which narrow or roughen the hollow locally, have been arranged in the feeder piece 12, such as one or more protrusions 25 extending inwards from the inner surface of the feeder piece 12. The purpose of these is to keep the tissue 2 inside the feeder piece 12 after it has been placed there. This facilitates the handling of the feeder piece 12, because from the point of view of grating it may be advantageous that the opening of the feeder piece faces downwards in the apparatus, but, on the other hand, the placing takes place more advantageously with the opening facing upwards.

FIG. 1 shows how a necessary force F (arrow) is directed during operation to the feeder piece 12 by means of a suitable pin 13 or corresponding feeding mechanism 110, in which case the feeder piece ensures that the tissue, together with the feeder piece, is in a disintegration connection with the grater surface 3.1.

FIG. 2 shows schematically another embodiment of the apparatus 100 according to the invention for mechanically disintegrating tissue into micrografts, which embodiment is similar to the one presented in FIG. 1 with the exception of the feeder piece 12. The apparatus comprises a blade part 3 with a planar grater surface 3.1 and a tissue holder 102 for supporting the tissue 2 and guiding it against the grater surface 3.1 of the blade part. The blade part 3 and the tissue holder 102 are arranged to be movable relative to each other, in which case the planar grater surface 3.1 is straight at least in the direction of the movement between the blade part 3 and the tissue holder 102. There are various ways in which to accomplish the relative movement between the blade part 3 and the tissue holder.

The tissue holder 102 also comprises a body part 104 in the embodiment according to FIG. 2. An elongated guide space 106 is arranged in the body part 104 for taking the tissue in a controlled manner against the grater surface 3.1. The guide space 106 has at least one guide surface 108, against which the tissue 2 is supported by means of a specific feeder piece 12. The guide surface is straight in its longitudinal direction X.

In FIG. 2, the tissue holder 102 of the apparatus 100 comprises a two-part feeder piece 12. The feeder piece 12 comprises a hollow cylindrical circumferential piece 12.1 and a bottom part 12.2 that serves as a push piece, which bottom part 12.2 is consequently movable relative to the circumferential piece in this embodiment. At the same time, the feeding mechanism 110 is implemented so that a force F1, F2 of a different magnitude can be directed to the different feeder pieces 12.1, 12.2 and the feeder pieces can also move relative to each other, which is illustrated in FIG. 2 in particular. Highlighted in FIG. 2 is a gap 112 between the blade part 3 and the body part 104. This shows how the feeder piece 12, in the embodiment of FIG. 2 its circumferential piece 12.1, prevents—being against the grater surface 3.1—the access of the tissue 2 into the gap 112, improving the functioning of the apparatus for the disintegration of tissue.

In this case it is possible to direct only such a force F2 to the circumferential piece 12.1 that the circumferential piece is in a close and sufficient contact with the blade part 3 preventing the escape of the tissue 2 into the gap 112, but at the same time the wear of the circumferential piece 12.1 is minimised. On the other hand, such a force a F1 is directed to the push piece 12.2 that it moves at a speed that is suitable in view of the disintegration of the tissue. The suitable forces can be determined easily using simple experimental tests.

By means of the push piece 12.2, the tissue 2 can be disintegrated completely by moving the push piece 12.2 all the way down to the grater surface 3.1, in which case a small portion of the push piece 12.2 becomes grated, but the actual feeding mechanism cannot come into contact with the blade part.

The basic solutions of FIG. 1 and FIG. 2 are applicable to all the technical ways of the invention to implement the apparatus in practice, in particular as presented in FIGS. 3-6.

In what follows, the invention is described by making reference to FIG. 3 and FIG. 4, which show a specific micro-grating tool 6, and FIG. 3 shows a rotating unit 5 related to it. The mechanical processing of tissue into micrografts requires a movement between the tissue and the grater surface, and a force that keeps the tissue and the grater surface in contact with each other, which here takes place by rotating a disc-like blade part 3, which has a grater surface 3.1. The blade here is circular, and it is supported in the centre to a rotating shaft. On the other side of the blade, there is a basin 9, and on the side opposite to the blade there is a tissue holder 102 and its body part 104, which is formed to be the cover structure 15 of the basin 9 so that the cover structure 15 and the basin 9 are fastened to each other in a detachable manner, closing the blade between them. The basin 9 and the cover structure are rotationally symmetrical, cylindrical pieces, where the cover part has a cover part that closes the circumferential part, and the basin has a bottom part that closes its circumferential part. In this embodiment, the movement between the blade part and the tissue holder is a rotatory movement.

The grater surface consists of one or more blade openings 4 or similar, the size, quantity and shape of which can be selected to suit the purpose. The blade opening 4 typically constitutes an opening in the blade part 3.1, but a blade opening can also refer to roughening structures or structures that enable grating otherwise and that extend from the surface plane of the blade part, even if they do not make an actual hole in the blade part 3. The blade opening is advantageously smaller than 100 μm.

The rotation of the blade part 3 that includes the grater surface 3.1 can be carried out by means of a rotating unit 5 specifically designed for this purpose, typically including an electric motor and gear to produce a suitable speed of rotation and torque. Transmission most advantageously takes place from below or from the side opposite to the blade part 3 with respect to the feeding direction of the tissue, utilising a shaft 10, in which case the transmission does not take up space at the top of the apparatus, in other words on the same side of the blade, where the tissue holder 102 is, and the upper part of the apparatus can be used more freely for feeding the tissue.

There can be an adapter 7 and/or a guard 8 between the rotating unit 5 and the actual micro-grating tool 6 (presented in full in FIG. 4), which adapter 7 and/or guard 8 enable that the use of the actual micro-grating tool 6 is sterile, while at the same time the rotating unit 5 is a multipurpose unit and can be non-sterile.

At the bottom part of the micro-grating tool 6, there is a basin space 9, into which the grated tissue suspension is collected. The blade part 3 comprising the grater surface 3.1 can be lowered lower into the basin space 9 by means of an expedient design of the shaft 10 or by means of an adapter part with a corresponding design.

This enables that the basin space 9 can be filled with liquid before the starting of processing so that the grater surface 3.1 is at the level of the liquid surface or below it. In this case, the biological tissue does not stick to the blade part 3 as it would to a dry grater surface 3.1.

The tissue 2 is fed to the blade part along a channel 11 formed in the body part 104, which channel 11 forms a guide space (cf. FIG. 1 and FIG. 2). The lower edge of the channel 11 is close to the grater surface 3.1, but, considering manufacturing tolerances and various forces and movements caused by operation, still so far that the lower edge of the channel 11 does not come into contact with the blade part. In other words, there is a gap 112 between the channel 11 and the blade part 3, but the channel 11 supports the feeder piece 12 close to the grater surface 1.

The tissue 2 is pressed against the grater surface 1 by utilising the feeder piece 12, which is made from a suitable sacrificial material. Sacrificial material here means any material that is intended to be grated along. The sacrificial material, in other words the feeder piece 12 made from it, is therefore sacrificed as part of its intended purpose. When the feeder piece made from the sacrificial material is designed to be hollow, it is in contact with the grater surface 3.1 by its edges, in other words by the cross-sectional circumference, and is grated intentionally along, at the same time preventing the tissue 2 from escaping with the grater surface 3.1 as a result of the forces caused by grating. When the feeder piece 12 is being grated, the tissue 2 has no alternative other than to be grated along. Hollow means that the feeder piece surrounds the tissue 2 from at least two directions. The space bordered by the feeder piece 12 can be referred to as a hollow 14.

The feeder piece 12 must be mechanically sufficiently strong, and its negative impacts on the cells of the tissue 2 should be minimal. The feeder piece 12 is most advantageously made from a material or materials that are used in pharmaceutical tablets as non-active substances and that have no negative impacts on the functioning of the cells. Such substances can be different types of sugars, salts, calcium, and fillers of pharmaceuticals. The cells and micrografts can also be isolated from the cell suspension by means of centrifugation, for example, in which case the feeder piece materials can also be washed away largely from the cells. FIG. 7 shows one embodiment of the feeder piece. Here, the feeder piece 12 is cup-like, comprising an elongated cylindrical wall and an end piece, which closes the feeder piece hollow from its one end. Advantageous or sought-after features of the feeder piece 12 include: preservability, processibility, minimisation of friction and good separation of the sacrificial material of the feeder piece from the tissue suspension. A person skilled in the art is capable of selecting suitable materials and a suitable method of manufacture (such as shape of moulds, the force directed to them, temperature) based on that person's knowledge and simple tests.

Above-mentioned non-active substances have been described in, among others: "Handbook of Pharmaceutical Excipients: Edition 9 9th Revised edition by Paul J Sheskey (Editor), Bruno C Hancock (Editor), Gary P Moss (Editor), David J Goldfarb (Editor)".

The feeder piece 12 can be pressed manually by means of a separate pin 13, which is dimensioned most advantageously so that when the pin is at the bottom, the hollow 14 of the feeder piece 12 and the tissue 2 that was in the hollow 14 of the feeder piece 12 have become completely ground, but some of the feeder piece 12 is still remaining and the pin 13 is not in contact with the grater surface 1.

When the tissue has been processed, the cover structure 15 can be removed and the blade part can be lifted off using a handle 16, which is an extension of the shaft 10 or otherwise connected to the blade part 3. After this, the tissue suspension can be sucked or poured away for further treatment. An easy opening of the structure enables an easy examination and handling of the tissue suspension.

FIG. 5 and FIG. 6 show embodiments where the movement between the blade part and the tissue holder is linear. Here, the blade part 3 comprising the grater surface 3.1 remains stationary, and the tissue holder is moved by hand or otherwise. In this embodiment, the tissue holder can also be referred to as a feeding stick. The feeding stick 102 includes a feeding mechanism 110, which comprises a spring 111 to direct a suitable force to the feeder piece 12 and to the tissue 2. The purpose of the feeding mechanism 110 is to use the spring 111 to press the feeder piece 12 and consequently the tissue 2 against the grater surface 3.1 of the blade part 3. When the feeding stick 102 is moved, the tissue becomes gradually grated. It is possible and advantageous to vary the method of implementation of this embodiment so that the feeder piece 12 cannot push out of the feeding mechanism 110 or from the feeding stick 102 before the feeding mechanism 110 or the feeding stick 102 has been placed against the grater surface 3.1. This can be implemented by means of various locking solutions of the feeding mechanism, such as by means of a pin 20, which is pushable through the body part into an opening arranged in the feeding mechanism. In this embodiment, too, there can be a channel 11 that supports the feeder piece and that forms the guide space, which channel 11 becomes positioned suitably over the grater surface 3.1 and fastens to the body, for example, in the manner described in the embodiment of FIG. 3 or by being supported to a slide surface 22 positioned over the grater plane. The advantage of this embodiment is that no external source of power is needed, which makes the apparatus technically simpler and hence, among other things, decreases the manufacturing costs.

All of the above-described embodiments can further be modified in accordance with FIG. 6 so that the feeder piece 12 has two parts, consisting of a circumferential piece 12.1 and of a push piece 12.2. At the same time, the feeding mechanism 110 is implemented so that a force of a different magnitude is directed to the different feeder pieces 12.1, 12.2, and the feeder pieces can also move relative to each other. In this case, only such a force can be directed to the circumferential piece 12.1 that the piece is in a close contact with the blade part 3 preventing the escape of the tissue 2, but the wear of the feeder piece 12 is minimised. On the other hand, the push piece 12.2 can be moved so that the tissue becomes ground. It is advantageous to dimension the feeding mechanism so that the tissue becomes grated completely, a minor portion of the push piece 12.2 becomes grated, but the feeding mechanism cannot get involved in the blade part. The advantage of this implementation is the minimisation of the ground sacrificial material of the feeder piece. Moreover, when implemented suitably, it is possible that the tissue 2 can also be placed inside the feeder piece 12 from an end other than that where the grater surface 3.1 is, which may facilitate the handling of the tissue 2.

It may also be expedient to fasten the tissue pieces inside the feeder piece 12 by means of tissue adhesive, blood or autologous blood product to improve the grating result. This facilitates their handling and makes grating more controlled.

Post-gnawing, in other words the grating of tissue 2 that has become stuck to the grater surface 3.1 or that has otherwise been grated incompletely, at the end is possible if the feeder piece 12 is dimensioned so that some of the base portion of the feeder piece is still available for post-gnawing after the tissue 2 and the hollow 14 have become grated.

It is to be noted that what has been described above only includes some most preferred embodiments of the invention. It is therefore clear that the invention is not limited to the above embodiments alone, but it can be applied in many ways within the enclosed patent claims. The features described in conjunction with the various embodiments can also be used within the basic idea of the invention in conjunction with the other embodiments and/or various entities can be combined of the features presented if this is to be desired and if the technical facilities for this exist.

Numbered list of embodiments according to the invention:

1. An apparatus for mechanically disintegrating tissue into micrografts, which apparatus comprises the following that are movable relative to each other:
   a blade part with a grater surface, and
   a tissue holder for supporting the tissue and for guiding it against the grater surface,
   characterised in that the tissue holder comprises
   a guide space, which is arranged in the body part of the tissue holder, which guide space has at least one internal guide surface that is straight in the longitudinal direction of the guide space, which guide surface is at an angle with respect to the grater surface, and
   a tissue feeder piece, which is arranged in the guide space to be movable in the longitudinal direction, and that the feeder piece comprises a hollow that is open at least from the grater surface side end, into which hollow the tissue is placeable, and where the feeder piece is made from a sacrificial material, in which case it is arranged to be grated at least partially into the micrograft obtained from the tissue, when the apparatus is used for disintegrating tissue.
2. An apparatus according to embodiment 1 for mechanically disintegrating tissue into micrografts, characterised in that the grater surface is planar.
3. An apparatus according to embodiment 1 or 2 for mechanically disintegrating tissue into micrografts, characterised in that a body part is arranged to be at a distance from the grater surface, and the feeder piece is, when the apparatus is in operation, arranged against the grater surface.
4. An apparatus according to embodiment 1 for mechanically disintegrating tissue into micrografts, characterised in that the guide space and its guide surface are cylindrical, and that the feeder piece has a cylindrical outer surface.
5. An apparatus according to embodiment 1 for mechanically disintegrating tissue into micrografts, characterised in that the guide space and its guide surface have a cross section of a polygon, and that the outer surface of the feeder piece has a cross section of a polygon.

6. An apparatus according to embodiment 1 for mechanically disintegrating tissue into micrografts, characterised in that the feeder piece comprises one or more walls, which define the hollow inside the feeder piece.

7. An apparatus according to embodiment 1 for mechanically disintegrating tissue into micrografts, characterised in that the feeder piece comprises one or more walls in the direction of the guide space, and an end part at the end opposite to the end on the side of the grater surface.

8. An apparatus according to embodiment 7 for mechanically disintegrating tissue into micrografts, characterised in that the end part is a fixed part of the feeder piece.

9. An apparatus according to embodiment 1 for mechanically disintegrating tissue into micrografts, characterised in that the feeder piece comprises a hollow cylindrical circumferential piece (12.1) and a push piece (12.2), in which case the hollow of the feeder piece is cylindrical, and that the push piece is arranged to be movable inside the hollow of the circumferential piece in the longitudinal direction.

10. An apparatus according to embodiment 9 for mechanically disintegrating tissue into micrografts, characterised in that the apparatus comprises a feeding mechanism for directing a force to the feeder piece, which feeding mechanism is arranged to direct a force of a different magnitude to the push piece and to the circumferential piece.

11. An apparatus according to embodiment 7 for mechanically disintegrating tissue into micrografts, characterised in that one or more protrusions extending inwards from the surface are arranged on the inner surface of the hollow of the feeder piece.

12. An apparatus according to any one of the preceding embodiments 1 for mechanically disintegrating tissue into micrografts, characterised in that the apparatus comprises a feeding mechanism for directing a force to the feeder piece.

13. An apparatus according to embodiment 9 for mechanically disintegrating tissue into micrografts, characterised in that the parts of the feeder piece are of the same material.

14. An apparatus according to embodiment 9 for mechanically disintegrating tissue into micrografts, characterised in that the parts of the feeder piece are of different materials.

15. An apparatus according to any one of the preceding embodiments 1-14 for mechanically disintegrating tissue into micrografts, characterised in that the feeder piece is made from a material or materials that are used in pharmaceutical tablets as non-active substances and that have no negative impacts on the functioning of the cells.

16. An apparatus according to any one of the preceding embodiments 1-14 for mechanically disintegrating tissue into micrografts, characterised in that the feeder piece is made from a material that comprises one or more of the following: hypromellose, gelatine, various sugars, salts, calcium, and fillers of pharmaceuticals.

17. An apparatus according to any one of the preceding embodiments 1-14 for mechanically disintegrating tissue into micrografts, characterised in that the tissue is fastened to the feeder piece by means of tissue adhesive, blood or autologous blood product that contains coagulation factors.

18. A method for mechanically disintegrating tissue into micrografts, where the blade part, which has a planar grater surface, and the tissue placed in the tissue holder are made to move relative to each other, and where the tissue is guided against the grater surface, characterised in that the tissue is guided against the grater surface together with the tissue feeder piece so that the feeder piece is disintegrated together with the tissue.

19. A method according to embodiment 18, characterised in that the feeder piece comprises one or more walls and an end part at the end opposite to the end on the side of the grater surface.

20. A method according to embodiment 18 for mechanically disintegrating tissue into micrografts, characterised in that the feeder piece is formed from more than one parts, comprising a circumferential piece and a push piece, and that such a force F2 is directed to the circumferential piece that the piece is in a close and sufficient contact with the blade part, and such a force F1 is directed to the push piece that it moves at a speed that is suitable in view of the disintegration of the tissue.

21. A method according to embodiment 18-20, characterised in that the tissue is disintegrated by pressing it against the grater surface until the bottom part, which belongs to the feeder piece, is in contact with the grater surface.

22. A method according to embodiment 18, characterised in that tissue that has become stuck to the grater surface is post-gnawed at the end of processing by moving the bottom part, which belongs to the feeder piece, against the grater surface.

23. A method according to embodiment 18-22, characterised in that the grater surface is lubricated by oil, grease or alcohol.

24. A method according to embodiment 18-23, characterised in that the cells and micrografts are isolated from the cell suspension and from the sacrificial material, for example, by dissolving the sacrificial material, or by removing the sacrificial material by washing partially or completely; most advantageously washing is carried out by adding salt solution into the micrograft—sacrificial material, by dissolving the sacrificial material into the salt solution and by separating the micrografts by centrifugation.

25. A feeder piece for use in an apparatus according to any one of the embodiments 1-17, characterised in that the feeder piece is a cylindrical piece, which comprises a cylindrical hollow, which is open from at least a first end, and an end part of the hollow, which end part plugs the hollow.

26. A feeder piece for use in an apparatus according to any one of the embodiments 1-17, characterised in that the feeder piece comprises a hollow cylindrical circumferential piece and a push piece, in which case the hollow of the feeder piece is cylindrical, and that the push piece is arranged to be movable inside the hollow of the circumferential piece in the longitudinal direction.

27. A feeder piece for use in an apparatus according to any one of the embodiments 1-17, characterised in that the feeder piece is of a material that comprises one or more of the following: various sugars, salts, calcium, and fillers of pharmaceuticals.

28. A feeder piece according to the embodiments 25 and 26.

29. A feeder piece according to the embodiments 25 and 27.

The invention claimed is:

1. An apparatus for mechanically disintegrating tissue into micrografts, comprising:
a blade part with a grater surface; and
a tissue holder for supporting the tissue and for guiding the tissue against the grater surface, wherein the tissue holder comprises:
a guide space arranged in a body part of the tissue holder, wherein the guide space has at least one internal guide surface that is straight in a longitudinal direction of the guide space, wherein the guide space is at an angle with respect to the grater surface; and
a tissue feeder piece arranged in the guide space and movable in the longitudinal direction, the tissue feeder piece defining a hollow, into which the tissue is placeable, wherein the tissue feeder piece is made from a sacrificial material and is arranged to be grated at least partially into a micrograft obtained from the tissue when the apparatus is used for disintegrating tissue.

2. The apparatus according to claim 1, wherein the grater surface is planar.

3. The apparatus according to claim 1, wherein the body part is arranged to be at a distance from the grater surface, and the tissue feeder piece is, when the apparatus is in operation, arranged against the grater surface.

4. The apparatus according to claim 1, wherein the guide space and the at least one internal guide surface are cylindrical, and wherein the tissue feeder piece has a cylindrical outer surface.

5. The apparatus according to claim 1, wherein the tissue feeder piece comprises one or more walls which define the hollow inside the tissue feeder piece.

6. The apparatus according to claim 1, wherein the tissue is placeable into the hollow from an open end of the hollow.

7. The apparatus according to claim 1, wherein the tissue feeder piece comprises one or more walls in the direction of the at least one internal guide surface of the guide space.

8. The apparatus according to claim 7, further comprising an end part fixed to the tissue feeder piece.

9. The apparatus according to claim 1, wherein the tissue feeder piece comprises a hollow cylindrical circumferential piece and a push piece, wherein the hollow of the tissue feeder piece is cylindrical, and wherein the push piece is arranged to be movable inside the hollow of the circumferential piece in the longitudinal direction.

10. The apparatus according to claim 9, further comprising a feeding mechanism for directing a first force to the tissue feeder piece, which and wherein the feeding mechanism is arranged to direct a second force of a different magnitude to at least one of the push piece or the circumferential piece.

11. The apparatus according to claim 1 further comprising a feeding mechanism for directing a force to the tissue feeder piece.

12. The apparatus according to claim 1, wherein the tissue feeder piece is made from at least one of hypromellose, gelatine, sugar, salts calcium, and fillers of pharmaceuticals.

13. A method for mechanically disintegrating tissue into micrografts, wherein the method comprises:
providing a blade part with a planar grater surface; and
a tissue holder for supporting the tissue and for guiding the tissue against the grater surface, wherein the tissue holder comprises a guide space arranged in a body part of the tissue holder, wherein the guide space has at least one internal guide surface that is straight in a longitudinal direction of the guide space, wherein the guide space is at an angle with respect to the grater surface; and
a tissue feeder piece is arranged in the guide space and movable in the longitudinal direction, the tissue feeder piece defining a hollow, into which the tissue is placeable, wherein the tissue feeder piece is made from a sacrificial material, and is arranged to be grated at least partially into a micrograft obtained from the tissue; and
positioning tissue in the tissue holder such that the tissue is movable relative to the tissue holder;
utilizing the tissue feeder piece to guide the tissue into contact with the planar grater surface of the blade part, wherein the tissue feeder piece is made from a sacrificial material; and
disintegrating a portion of the tissue feeder piece and the tissue.

14. The method according to claim 13 wherein the tissue is disintegrated by pressing the tissue against the planar grater surface until a bottom part of the tissue feeder piece is in contact with the planar grater surface.

15. The method according to claim 13 wherein the tissue feeder piece includes a circumferential piece and a push piece, and wherein the method further comprising directing a first force to the circumferential piece to maintain the tissue feeder piece is in close and sufficient contact with the planar grater surface of the blade part, and directing a second force to the push piece such that the push piece moves at a speed that is suitable in view of the disintegration of the tissue.

16. The method according to claim 13, further including adding a solution between the blade part and the tissue feeder piece to reduce the friction therebetween, wherein the solution includes at least one of salt, alcohol, oil, grease, or a biocompatible liquid that does not dissolve into water.

17. The method according to claim 16, wherein the sacrificial material is of a water-soluble material.

18. The method according to claim 16, wherein the solution is separated after grating from a water-based micrograft mixture.

19. The method according to claim 18, wherein the separation of the solution from the water-based micrograft mixture is performed by a at least one of centrifugation, extraction, or dissolution.

20. The method according to claim 13, further comprising post-gnawing residual tissue using a bottom part of the tissue feeder piece.

* * * * *